(12) United States Patent
Marterstock

(10) Patent No.: US 11,819,598 B2
(45) Date of Patent: Nov. 21, 2023

(54) APPARATUS AND METHOD FOR REGENERATING A DIALYSIS SOLUTION

(71) Applicant: Fresenius Medical Care Deutschland GmbH, Bad Homburg (DE)

(72) Inventor: Stefan Konrad Marterstock, Dettelbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 222 days.

(21) Appl. No.: 16/978,247

(22) PCT Filed: Mar. 4, 2019

(86) PCT No.: PCT/EP2019/055338
§ 371 (c)(1),
(2) Date: Sep. 4, 2020

(87) PCT Pub. No.: WO2019/170613
PCT Pub. Date: Sep. 12, 2019

(65) Prior Publication Data
US 2020/0405938 A1  Dec. 31, 2020

(30) Foreign Application Priority Data

Mar. 6, 2018 (DE) ................ 10 2018 105 120.4

(51) Int. Cl.
*A61M 1/16* (2006.01)
*A61M 1/26* (2006.01)
(Continued)

(52) U.S. Cl.
CPC .......... *A61M 1/1696* (2013.01); *A61M 1/267* (2014.02); *A61M 1/3624* (2013.01);
(Continued)

(58) Field of Classification Search
CPC ........ A61M 1/16; A61M 1/1696; A61M 1/34; A61M 1/267; A61M 1/3624; A61M 1/282;
(Continued)

(56) References Cited

U.S. PATENT DOCUMENTS 7,169,352 B1 * 1/2007 Felt ..................... A61M 1/3639
210/741
9,700,663 B2 * 7/2017 Burbank .................. C02F 1/44
(Continued)

FOREIGN PATENT DOCUMENTS

KR   2-170090904 A  *  8/2017  .............. A61M 1/16
WO   WO2006/088419        8/2006
(Continued)

OTHER PUBLICATIONS

English machine translation of DE-102014017399-A1 (including patent); May 2016; Voelker; A61J3/00; 36 pages. (Year: 2016).*
(Continued)

*Primary Examiner* — Magali P Slawski
*Assistant Examiner* — Robin S Gray
(74) *Attorney, Agent, or Firm* — Jacobson Holman PLLC

(57) ABSTRACT

The present invention relates to an apparatus for regenerating a dialysis solution, wherein the apparatus has a first circuit and a second circuit, with the first circuit having a container for receiving the consumed dialysis solution, the primary side of a filter connected downstream of the container, and a return line from the primary side of the filter into the container, with the filter being configured to prepare purified water from the consumed dialysis solution, and with the second circuit having the secondary side of the filter, the dialyzate side of a dialyzer, and a return line from the (Continued)

Figure 1:
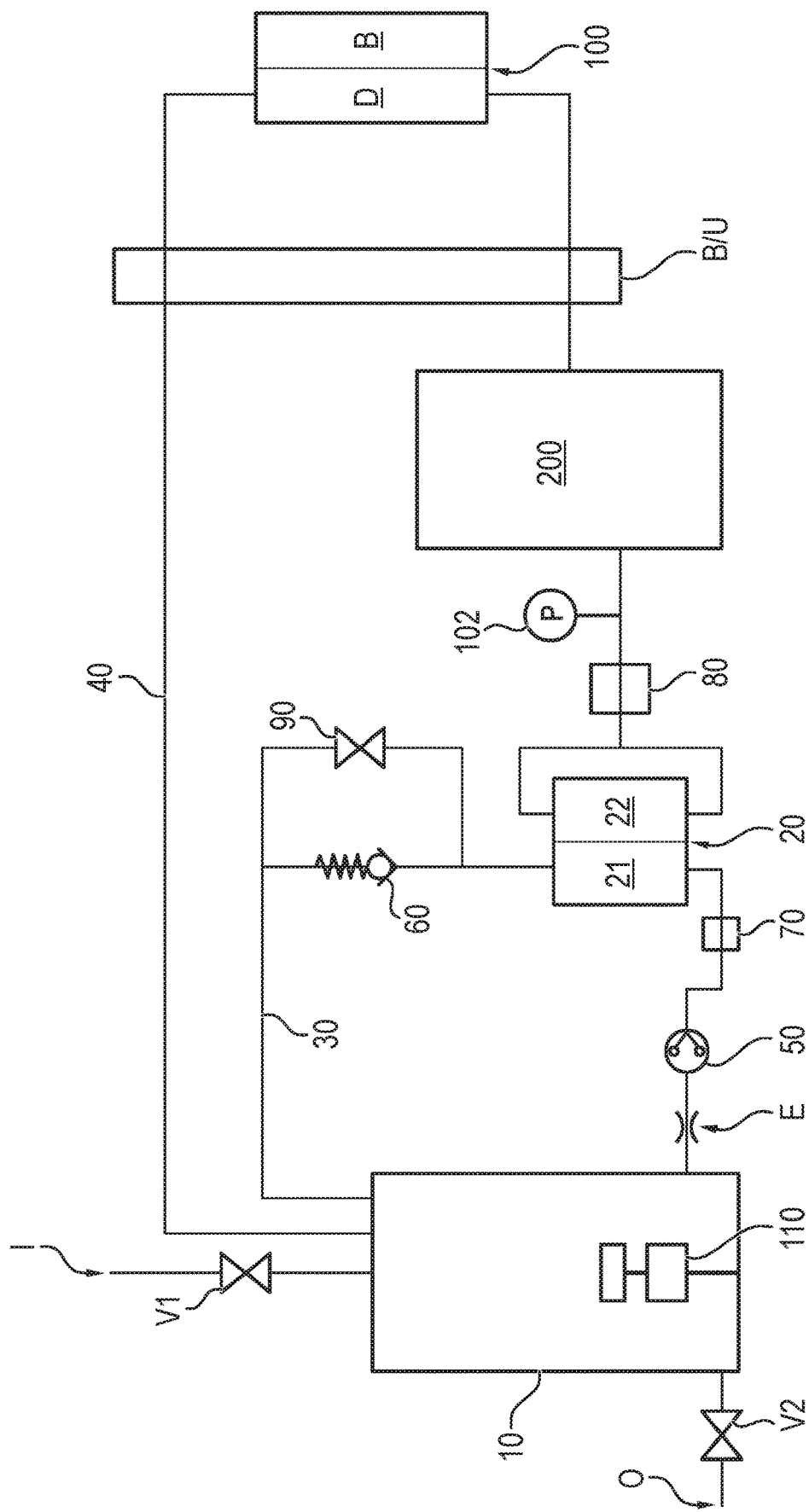

dialyzate side of the dialyzer into the container. The present invention further relates to a method of regenerating a dialysis solution.

12 Claims, 2 Drawing Sheets

(51) Int. Cl.
*A61M 1/36* (2006.01)
*B01D 71/02* (2006.01)
*A61M 1/28* (2006.01)

(52) U.S. Cl.
CPC ............ *B01D 71/021* (2013.01); *A61M 1/282* (2014.02); *A61M 2205/3327* (2013.01); *A61M 2205/3337* (2013.01); *A61M 2205/3386* (2013.01); *A61M 2205/50* (2013.01)

(58) Field of Classification Search
CPC ...... A61M 1/15; A61M 1/159; A61M 1/1657; A61M 1/3401; A61M 1/3622; A61M 1/3623; A61M 1/1672; A61M 1/1684; A61M 1/302; A61M 1/3465; A61M 1/3468; A61M 1/3482; A61M 1/3653; A61M 1/28; A61M 1/1692; A61M 2205/3327; A61M 2205/3337; A61M 2205/3386; A61M 2205/50; A61M 2205/3379; A61M 1/5622; A61M 1/3626; A61M 2205/3331; A61M 2205/3334; A61M 1/26; A61M 1/36; B01D 61/00; B01D 60/14; B01D 71/021; B01D 71/02; B01D 71/0211
See application file for complete search history.

(56) References Cited

U.S. PATENT DOCUMENTS

| | | | |
|---|---|---|---|
| 10,451,591 B1* | 10/2019 | Gebauer | F16K 7/07 |
| 2004/0232079 A1* | 11/2004 | Taylor | A61M 1/1666 |
| | | | 250/435 |
| 2011/0017665 A1* | 1/2011 | Updyke | A61M 1/1696 |
| | | | 210/96.2 |
| 2016/0213829 A1* | 7/2016 | Klewinghaus | A61M 1/1664 |
| 2017/0065762 A1* | 3/2017 | Larsen | A61M 1/1696 |
| 2018/0104399 A1* | 4/2018 | Dowell | B01D 63/10 |
| 2019/0225521 A1* | 7/2019 | Heath | C02F 1/48 |
| 2020/0129686 A1* | 4/2020 | Khawar | A61M 1/1603 |

FOREIGN PATENT DOCUMENTS

| | | | | |
|---|---|---|---|---|
| WO | WO2008/020801 | 2/2008 | | |
| WO | WO2015/124716 | 8/2015 | | |
| WO | WO-2017116515 A1 * | 7/2017 | ......... | A61M 1/1672 |
| WO | WO-2017137361 A1 * | 8/2017 | ........... | B01D 61/002 |

OTHER PUBLICATIONS

English machine translation of WO-2018041622-A1 (including patent); Mar. 2018; Kreber; A61M1/16; 55 pages. (Year: 2018).*
English machine translation of KR-20170090904-A; Aug. 8, 2017; Jeon; 6 pages. (Year: 2017).*

* cited by examiner

APPARATUS AND METHOD FOR REGENERATING A DIALYSIS SOLUTION

The present invention relates to an apparatus and to a method of regenerating a dialysis solution.

It is known from the prior art to supply dialysis machines with ultrapure water through an RO plant (RO=reverse osmosis). The ultrapure water is mixed with one or more concentrates to obtain a ready-to-use dialysis solution for the treatment of patients. The dialysis solution is enriched with substances to be removed from the blood of the patient in the dialyzer and is disposed off via an outflow. To be able to use the energy content of the consumed dialysis solution in part, it is furthermore known to transfer heat from the consumed dialysis solution to the ready-to-use dialysis solution by means of heat exchangers.

It is a disadvantage with these known system or dialysis machines that, due to the high water consumption for the preparation of the dialysis solution, they are necessarily large and heavy so that a transport of the machines is only possible with difficulty or not at all. This disadvantage plays a particular role, for example, in home hemodialysis. In addition, this equally applies to so-called portable machines that should enable a mobility for the patient during the treatment.

It is the underlying object of the present invention to further develop an apparatus of the initially named kind such that it can be designed as comparatively compact and has a smaller water and energy consumption in comparison with known apparatus.

This object is achieved by an apparatus having the features described below.

Provision is accordingly made that the apparatus has a first circuit and a second circuit, with the first circuit having a container for receiving the consumed dialysis solution, the primary side of a filter connected downstream of the container, and a return line from the primary side of the filter into the container, with the filter being configured to prepare purified water, preferably ultrapure water, from the consumed dialysis solution, and with the second circuit having the secondary side of the filter, the dialyzate side of a dialyzer, and a return line from the dialyzate side of the dialyzer into the container.

The filter has the object of preparing purified water from the solution contained in the container, i.e. water whose content or concentration of contaminants and other ingredients such as ions, molecules, is smaller than in the solution supplied to the filter. The filter is preferably configured to prepare ultrapure water, which is understood within the framework of the present invention as water that is suitable to be used for preparing a ready-to-use dialysis solution. The filter can be in one or multiple stages, with the plurality of stages being flowed through by solution one after the other. The use of a plurality of filters connected in series is also conceivable to obtain the desired degree of purity of the water. The filter is preferably an RO (reverse osmosis) filter, for example in the form of a winding module.

The apparatus preferably has one or more concentrate lines that open into the line conducting the ultrapure water or into a mixing region so that the ready-to-use dialysis solution can be prepared from the ultrapure water and the concentrate or concentrates and optionally further additives.

Said filter is preferably a graphene filter. A filter is understood by this that contains graphene or a graphene derivative such as graphene oxide as the filter material or whose filter material consists of or comprises these materials. Graphene or graphene oxide is gas-tight and water-permeable, which brings about the advantage within the framework of the present invention that a gas entry does not take place from the first into the second circuit and thus into the ready-to-use dialysis solution.

The present invention is, however, not restricted to these filters, but rather also comprises other filters that are preferably impermeable for gas, but allow liquid to pass.

If the filter used does not have this property of impermeability for gas, air can, for example, be separated at the primary side by a degassing restrictor and can then be conveyed via a valve (preferably a pressure relief valve) back into the container and can thus be removed.

A pump is preferably arranged in the first circuit, preferably upstream of the filter, to effect a flow of fluid in the first circuit. If this pump is adjustable in its conveying power or in its conveying pressure, the throughput of the solution through the first circuit and/or the pressure of the liquid on the primary side of the filter can be set to an optimum filter operating point by means of the pump.

A pressure relief valve by means of which the pressure on the primary side of the filter is adjustable is preferably located downstream of the filter in the first circuit. It can here, for example, be a pressure relief valve that can be adjustable. The pressure conditions on the primary side of the filter can also be set to the desired value or in a desired range in this manner.

A bypass line around the pressure relief device and closable by a blocking element can be provided in the first circuit. This can be required to flush the primary side of the filter free, with the blocking element being open and with the flow along the primary side of the membrane removing contaminants that are present there and that can e.g. be present as a film or layer.

A sensor, preferably a conductivity cell, can be arranged in the first circuit to detect the concentration of substances in the first circuit. It is thus possible to determine whether the concentration of substances has already adopted such a high value that a complete exchange of water is necessary in the total apparatus or at least in parts thereof such as in the container and/or in the first circuit and/or in the second circuit.

A sensor, preferably a conductivity cell, can be arranged in the second circuit before, i.e. upstream of the dialyzer, to determine the purity of the water of the filter present on the secondary side. If it is not within predefined limits or if it is below a limit value, a conclusion can be drawn on a defect of the filter. A controller can be present that recognizes this and advises the user accordingly and/or switches the apparatus off.

It is pointed out at this point that the terms "upstream" and "downstream" relate to the position of the components relative to one another when the apparatus is in operation, i.e. is flowed through by liquid.

A pressure measurement device can be arranged downstream of the secondary side of the filter. Indications of whether the filter is defective can likewise be acquired from the pressure measured there. Apart from this, how large the transmembrane pressure is that can then be set to a value ideal for the respective filter used can be determined with knowledge of the pressure on the primary side. This can take place, for example, by a pump that is arranged at the primary side and that is arranged upstream of the filter in the first circuit.

It is furthermore conceivable that a mixing device is provided downstream of the secondary side of the filter that is configured to supply one or more concentrates for preparing a ready-to-use dialysis solution to the water flowing off from the secondary side of the filter. One or more concentrate lines can be provided for this purpose that lead to the mixing device and that can be connected to concentrate containers or to which concentrate containers are connected.

In a further embodiment of the invention, the apparatus has an ultrafiltration pump for removing dialysis solution, preferably from the return line, to be able to realize the liquid loss of the patient that is desired or is prescribed by the physician.

In a variant, the apparatus has a balancing chamber for the balanced supply and removal of dialysis solution to and from the dialyzer such as is known from the prior art. It is, however, alternatively also conceivable with this new concept to realize the balancing via the container of the first circuit; for example with the aid of a filling level sensor, which makes possible a simple setup of the apparatus.

As already stated above, it is of advantage if the filter is impermeable to gas. In this case, a degassing device in the second circuit can be dispensed with.

The apparatus preferably has a controller that is configured to partly or completely discard liquid located in the container or in one or both circuits or in the total apparatus and to replace it with fresh water when the sensor reports a value to the controller that exceeds a concentration limit value. This is the case when the solution is concentrated so much or has so many contaminants that a regeneration is not or is no longer sensibly possible.

A level sensor can be arranged in the container with provision preferably being made that the apparatus has a controller that is configured to output an error message and/or to stop the operation of the apparatus when the filling level in the container drops with respect to a starting value. If the first and second circuits are closed, which represents a preferred embodiment of the invention, a drop of the filling level in the container can only be due to a leak of the apparatus. The first and/or second circuits are preferably closed. It is to be understood by this that the first circuit leads from the container via the filters back to the container again and the second circuit leads from the filter via the dialyzer to the container from where the solution is again supplied to the filter.

Provision can be made in an embodiment that the container is designed as a bag, in particular as a flexible bag. This has the advantage that the volume of the container can be designed as flexible. Provision can additionally be made that the bag is designed as a disposable, i.e. as an article for single use. The container can thus be disposed of, optionally together with the filter and the dialyzer, in a simple manner after the end of the treatment. Only a small amount of waste is thus incurred in the design as a bag.

The apparatus can represent a component of a dialysis machine or can form a dialysis machine such as a peritoneal dialysis machine, a hemodialysis machine, or a hemodiafiltration machine.

The present invention further relates to a method of regenerating a dialysis solution having an apparatus as described herein, wherein the solution is supplied from the container to the primary side of the filter; the retentate is returned into the container; and the permeate is supplied to a mixing region of the apparatus in which a ready-to-use dialysis solution that is supplied to a dialyzer is prepared by the mixing of the permeate with one or more concentrates.

It is possible in dependence on the treatment process neither to supply fresh water to the container nor to drain off consumed solution during a therapeutic treatment. This is particularly important in mobile applications. A change of water preferably only takes place when the solution is concentrated so much that a regeneration is no longer possible or is only possible with a great effort. This can be necessary when the container is of a particularly small design so that a particularly high rate of recycling is required. Such embodiments can be particularly sensible in home dialysis. On a stationary application of the technical solution, a cyclic exchange of the liquid in the first and/or second circuits is possible (so-called fresh water cycling).

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment shown in the drawing.

Figure 2:
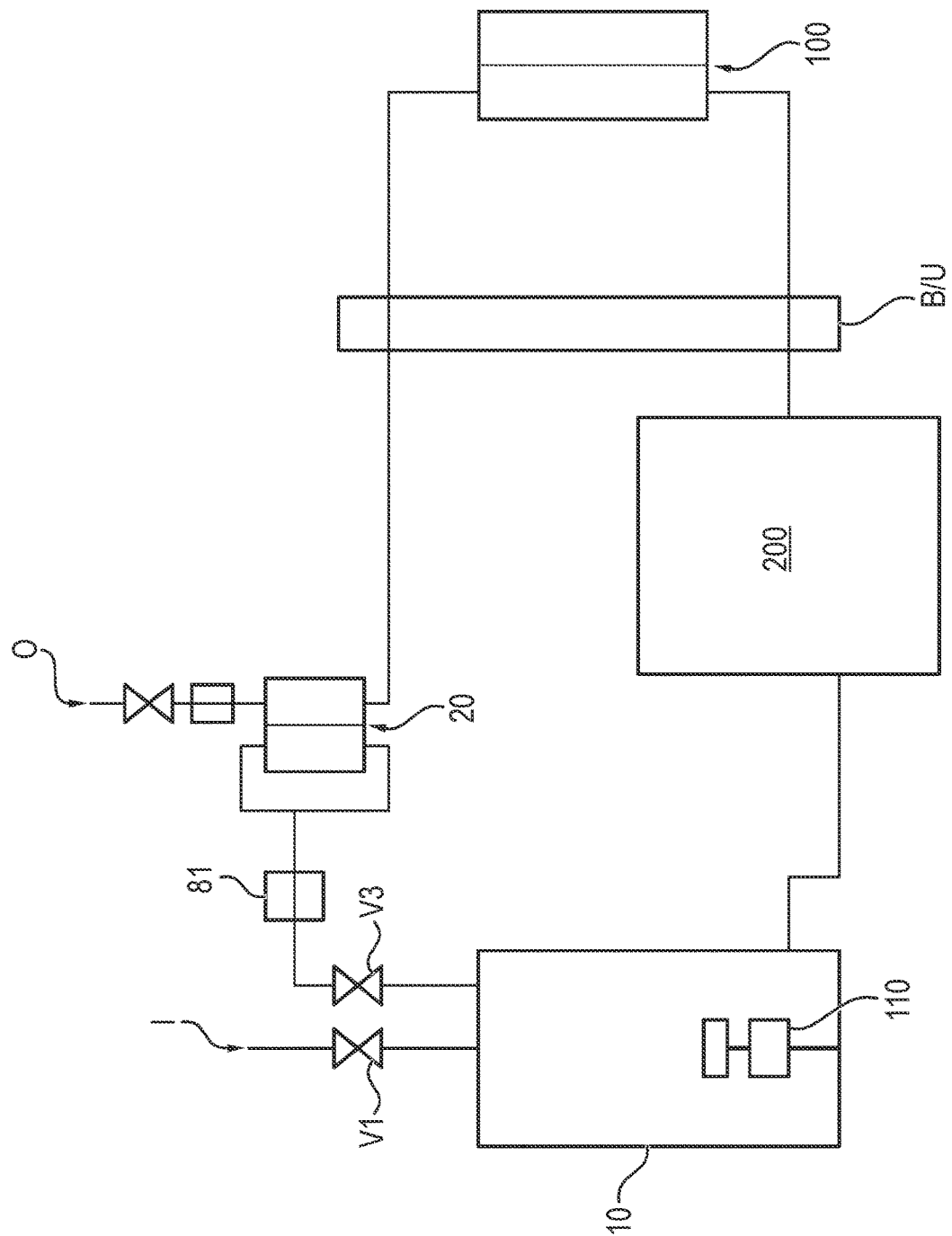

There are shown:

FIG. 1: a schematic flow diagram of an apparatus in accordance with the invention; and FIG. 2: a schematic flow diagram of a further apparatus that is not a subject of the invention.

FIG. 1 shows an apparatus in accordance with the invention. The inlet for fresh water into the container 10 is marked by reference symbol I, with the inlet line being blockable by a valve V1.

The drain from the container 10 for consumed solution is marked by O, with the drain line being blockable by a valve V2. The container 10 will also be called a water inlet chamber in the following.

A container 10 having a stationary water connection or also any other container such as a bag such as a dialyzate bag can generally be used.

The container 10 can have rigid or flexible walls.

Reference numeral 100 marks a dialyzer that preferably has a plurality of membranes, preferably a membrane bundle, that are flowed through by dialyzate on a one side D and by blood on the other side B. The dialysis solution that has flowed through the dialyzer 100 and is thus charged with contaminants from the blood is called consumed dialysis solution or consumed dialyzate.

The consumed dialyzate that is conducted from the dialyzer 100 through the line 40 back into the water inlet chamber 10 is sucked in by a pump 50 and is pumped into a circuit which is positioned upstream and which is the first circuit in the sense of the invention.

This circuit substantially comprises the pump 50, the container 10, the primary side of the filter 20, i.e. the section in front of the filter membrane or in front of another filter medium, and the pressure relief valve 60 including the lines connecting these components. Reference numeral 30 designates the return line from the valve 60 to the container 10.

Reference numeral 60 designates a pressure relief valve. The pump 50 conveys the consumed dialysis solution from the container 10 through the primary side 21 of the filter 20 via the valve 60 back into the container 10. A pressure drop arises over the valve 60 here and thus also over the filter 20. This pressure or pressure drop can be set by the valve 60 and can thus be coordinated with the ideal working point of the filter 20.

The pressure gradient between the primary side 21 and the secondary side 22 of the filter 20 has the result that a flow takes place through the filter membrane or through the other filter medium, with ultrapure water being present on the secondary side 22, i.e. after the filter medium. It enters into the mixing device 200 that can be designed as a mixing circuit, a mixing container, a line section, etc.

The mixing of the ultrapure water with one or more concentrates such as with a base concentrate and an acid concentrate takes place in the mixing circuit or mixing container, etc. The heating or post-heating of the dialysis solution can also take place there so that, where possible, no heat is withdrawn from the blood in the dialyzer 100 by the dialysis solution.

The retentate, i.e. that portion of the liquid that is not separated by the filter 20, remains on the primary side and moves over the valve 60 back into the water inlet chamber 10.

This has the consequence that the liquid in the container 10 is gradually further concentrated, whereby its electric conductivity increases.

As can be seen from FIG. 1, the first and second circuits are two closed, cascaded water circuits or liquid circuits. More than two of these circuits can generally also be present.

The filter 20 can inter alia be based on a graphene filter technique, whereby the ultrapure water can be simultaneously separated from the filter without dissolved oxygen. This saves further components in the dialysis machine such as a separate degassing circuit.

A high performance can be achieved by the "washing" of the filter 20 at its primary side 21 via the valve 60 and the contamination of the filter 20 can be prevented or delayed. The service life of the filter 20 is thereby increased. The filter 20 can additionally be flushed free in that the valve 90 short circuits the pressure relief valve 60. In this case, the liquid moves into the bypass that includes the valve 90 while bypassing the valve 60 and moves from there back into the container. This procedure is advantageous if the filter performance has noticeably dropped off.

As can further be seen from FIG. 1, a filling level sensor 110 is located in the container 10. If this reports that the filling level in the container 10 has fallen below a limit value, a conclusion can be draw on a leak since both the first circuit and the second circuit are closed and the filling level would thus have to remain the same. The valves V1 and V2 are closed in normal operation, i.e. when no change of water takes place.

The presence of a conductivity cell 70 after, i.e. downstream, of the pump further results from FIG. 1. The concentration of the contaminated liquid caused by the circuit operation is thus measurable and when the water in the circuit should be completely replaced (fresh water cycling) can thus be derived. This exchange can take place by using the valves V1 and V2 and can be volumetrically balanced with the aid of the level sensor 110 in the container 10.

In normal dialysis operation, the valves V1 and V2 are closed, whereby the level sensor 10 can be used, as stated, as leak monitoring. If one of the two closed circuits loses liquid, this is detectable with reference to the level in the container 10. This serves patient safety.

The function of the filter 20 can be monitored by a further conductivity cell 80 after, i.e. downstream of, the filter 20. As soon as relevant damage to the filter membrane or to another filter medium is present, conducive ions pass through the filter 20 that can in turn be detected by the sensor 80.

Optionally, the transmembrane pressure can be monitored over the filter 20 by means of the pressure sensor 102 arranged downstream of the filter 20 to be able to determine a degradation or loss of performance of the filter.

Since the two circuits are closed, the energy requirements for the heating of the dialyzate falls considerably. As a consequence, smaller heating devices can be used than is the case with machines known from the prior art. A heat exchanger is admittedly optionally conceivable for the fresh water cycling, but can also be dispensed with for cost reasons.

As stated above, the ultrapure water arising at the secondary side 22 of the filter 20 moves into the mixing part 200 of the machine and is there e.g. enriched with bicarbonate and acid so that a ready-to-use dialysis liquid is available at the dialyzer 100 for exchange with the blood of the patient.

Reference symbol B/U marks the balancing unit and/or an ultrafiltration pump that withdraws a partial volume from the consumed dialysis liquid corresponding to the prescription by the physician.

Toxic substances that are larger than water can still be removed from the patient by the two-stage (cascaded) filter attachment. These substances, also including ions such as Na and Cl from the dialysis liquid are subsequently concentrated in the container 10 and are discarded via the outflow O as part of the fresh water cycling. The ultrafiltration still e.g. takes place via a UF pump in the unit B/U that conveys directly into the drain. Since the circuits are closed circuits, the advantages of volumetric balancing such as today, for example, takes place with the aid of a balancing chamber can be maintained.

The requirement for additional degassing measures/degassing apparatus is dispensed with in this design due to the properties of the filter 20 to be impermeable or gases. Alternatively, if required, depending on the filter used, a degassing restrictor/degassing apparatus can also be introduced into the upstream circuit, i.e. the first circuit, such as is shown by reference symbol E in FIG. 1. The filter module 20 or also a separate air separation chamber that can, for example, be arranged between 20 and 60 in FIG. 1 can serve as an air separation chamber here.

FIG. 2 shows a variant that is not a subject of the protective scope of the invention. Elements that are the same or have the same function have the same reference numerals as in FIG. 1.

As can be seen from FIG. 2, consumed dialyzate is supplied to the filter 20 after flowing through the dialyzer 100 to separate pure water that is conveyed back into the water inlet chamber 10. The retentate is discarded via the drain O. The conductivity of the pure water is measured in the conductivity sensor 81 and the pure water moves into the container 10 with an open valve V3. It is disadvantageous in this concept that the filter 20 is not washed over at all times, whereby there is a risk that the filter 20 clogs considerably faster, i.e. loses performance. This can optionally only be avoided in that an increased water portion is discarded over the drain O, which increases the water consumption and makes mobile applications impossible. The concentrated liquid can still only collect in the filter 20 itself, which makes a measurement by means of a conductivity cell more difficult to temporally control the fresh water cycling, i.e. the exchange of the liquid in the closed circuit.

A further disadvantage of the arrangement in FIG. 2 is the pressure situation in the circuit. The transmembrane pressure over the filter is transmitted back to the dialysis filter without any further components and said dialysis filter is in contact with the patient. For this reason, further components such as free drop distances, pressure reducers and/or also pumps are necessary to set up such a system. This is not the case in the arrangement in accordance with FIG. 1 since the pressure side, i.e. the primary side 21 of the filter 20, is not in direct communication with the dialyzer 100, but the secondary side 22.

An inexpensive design of a dialysis machine that can be designed as compact and easily transportable can be implemented in accordance with the invention with relatively few components. This could permit longer dialysis treatments with a reduced dialyzate flow and blood flow, which is positive both for the compatibility of the treatment and for the life expectancy of the patient since it comes closer to the natural function of the kidney.

Advantages of preferred embodiments of the present invention not restricting the invention are:

An integrated degassing is possible which is dependent on the filter properties or on the graphene filter technique used;

An integrated balancing by closed circuits is possible, with two or more circuits being arranged in cascaded form;

The RO system is integrated, a saving of components, i.e. costs and construction size, thus results;

Only one pressure pump is necessary to wash over the filter and also to build up pressure for the mixing arrangement to prepare the ready-to-use dialyzate; a further pump can thus be saved;

There is no direct, unwanted return pressure effect on the patient over the dialyzer since the primary side of the filter is separated from the dialyzer by the membrane;

The filter can be washed over; increased service lives thereby result;

The pump does not run in RO water, which is accompanied by an increased service life of the pump;

There is a lower water consumption and thus also energy consumption for heating in comparison with today's machines;

An automatic check for leaks is possible via the level sensor in the container since a leak results in a low water alarm/a falling below of an alarm level in the container;

The functional capability of the filter can be monitored in a technical safety manner, and indeed with a conductivity cell or the like arranged downstream of the filter. It is thus ensured that the correct composition of the dialyzate can be achieved in the following mixing apparatus of the machine:

A time control of when the liquid in the circuit has to be replaced is possible with the conductivity cell that comes into contact with the consumed solution (fresh water cycling); the flushing cycle can likewise be determined by means of this conductivity cell;

It is a compact, inexpensive machine concept;

The balancing of the liquid content of the patient is simplified by closed circuits;

A simple and extremely accurate ultrafiltration is possible;

A highly sterile starting liquid for the mixing device of the dialysis machine can be prepared;

The apparatus can be used in peritoneal dialysis (PD) machines and in hemodialysis (HD) machines or can form them. The apparatus can represent a dialysis machine or a part thereof.

Various combinations with the components in accordance with FIG. 1 are also conceivable.

The pump 50 is thus optional, for example.

The sensor 70 can also be replaced by a fixed control, i.e. fixed fresh water cycling processes/flushing processes of the filter.

The degassing apparatus E can also be present or omitted depending on the filter used.

The pump 50 could also be arranged in front of or behind the sensor 80; however, no washing over is possible in this configuration and the problems of FIG. 2 would result that are accompanied by a performance loss of the filter.

A further pump on the output side (secondary side) of the filter in front of or behind the sensor 80 or in the line 40 or within the B/U unit would, however, also be conceivable.

The heating can be provided both in the first circuit and in the second circuit.

A pump for conveying the dialysis solution or the ultrapure water is preferably also present in the second circuit.

The concept in accordance with FIG. 1 preferably uses the graphene filter technique; but the invention is neither restricted to this nor to another specific filter. Other technologies are also conceivable with the concept in FIG. 1 or in accordance with the invention if these membranes are able to separate water/ultrapure water from contaminated liquid, RO filter systems known from the prior art are typically based on a different technique. They are typically winding modules having a poor performance in comparison, but these filters are also conceivable as filters 20.

The invention claimed is:

1. An apparatus for regenerating a dialysis solution, the apparatus comprising a first circuit and a second circuit, with the first circuit having a container for receiving a consumed dialysis solution, a primary side of a graphene filter connected downstream of the container, a valve located downstream of the primary side of the filter, and a return line from the primary side of the filter into the container, with the filter being configured to prepare ultrapure water from the consumed dialysis solution, with the container configured to separate toxic substances from the consumed dialysis solution, with the first circuit configured to move retentate remaining on the primary side of the filter through the return line over the valve and into the container, and with the second circuit having a secondary side of the graphene filter, a dialyzate side of a dialyzer, and a return line from the dialyzate side of the dialyzer into the container.

2. An apparatus in accordance with claim 1, characterized in that a pump is arranged in the first circuit upstream of the primary side of the filter to effect a flow of liquid in the first circuit; and in that the valve is a pressure relief valve by which pressure can be set on the primary side of the filter.

3. An apparatus in accordance with claim 2, characterized in that a bypass line closable by a blocking element is provided around the pressure relief valve.

4. An apparatus in accordance with claim 1, characterized in that a first conductivity cell sensor is arranged in the first circuit to detect a concentration of substances in the first circuit; and/or characterized in that a second conductivity cell sensor is arranged upstream of the dialyzer in the second circuit to determine purity of water present on the secondary side of the filter.

5. An apparatus in accordance with claim 1, characterized in that a pressure measurement device is arranged downstream of the secondary side of the filter.

6. An apparatus in accordance with claim 1, characterized in that a mixing device is provided downstream of the secondary side of the filter that is configured to mix water flowing off from the secondary side of the filter with one or more concentrates for preparing a ready-to-use dialysis solution.

7. An apparatus in accordance with claim 1 further comprising an ultrafiltrate pump for conveying consumed dialysis solution from the dialyzer through a dialyzer return line to the container, and/or further comprising a balancing chamber (B) for balanced supply and removal of the regenerated dialysis solution and the consumed dialysis solution, respectively, to and from the dialyzer, respectively.

8. An apparatus in accordance with claim 1, characterized in that the filter is impermeable to gas; and/or in that the second circuit does not have a degassing device.

9. An apparatus in accordance with claim 4 further comprising a controller configured to partially or completely discard liquid contained in the container and to replace the liquid with fresh water when the first conductivity cell sensor reports a value to the controller that exceeds a concentration limit value.

10. An apparatus in accordance with claim 1 further comprising a level sensor arranged in the container and a controller configured to output an error message and/or to stop operation of the apparatus when a filling level in the container drops with respect to a starting value.

11. An apparatus in accordance with claim 1, characterized in that the first and/or second circuits are closed.

12. An apparatus in accordance with claim 1, characterized in that the container is a single-use, disposable flexible bag, and/or characterized in that the apparatus forms a dialysis machine or a part of a dialysis machine.

* * * * *